United States Patent [19]

Adler-Golden et al.

[11] Patent Number: 5,062,707
[45] Date of Patent: Nov. 5, 1991

[54] SURFACE CONTAMINATION SENSOR

[75] Inventors: Steven Adler-Golden, Newtonville; Michael W. Matthew, Burlington, both of Mass.

[73] Assignee: Spectral Sciences, Inc., Burlington, Mass.

[21] Appl. No.: 609,875

[22] Filed: Nov. 6, 1990

[51] Int. Cl.⁵ .................. G01N 21/71; G01N 21/88
[52] U.S. Cl. ................................ 356/311; 356/318; 356/237
[58] Field of Search ............... 356/237, 311, 313, 316, 356/318

[56] References Cited

U.S. PATENT DOCUMENTS 4,309,187 1/1982 Dodge, III et al. ............... 356/316

Primary Examiner—Vincent P. McGraw
Attorney, Agent, or Firm—Iandiorio & Dingman

[57] ABSTRACT

An ambient surface contamination sensor including a source for supplying gas, which is energized before it reaches the surface being sensed so that it is capable of transferring energy to the contaminants on the surface or vapor originating therefrom. The sensor then detects the optical emission from the gas passed over the surface within a selected wavelength band characteristic of the presence on the surface of the contaminant, and indicates the presence of the contaminant on the surface when such an emission is detected.

23 Claims, 3 Drawing Sheets

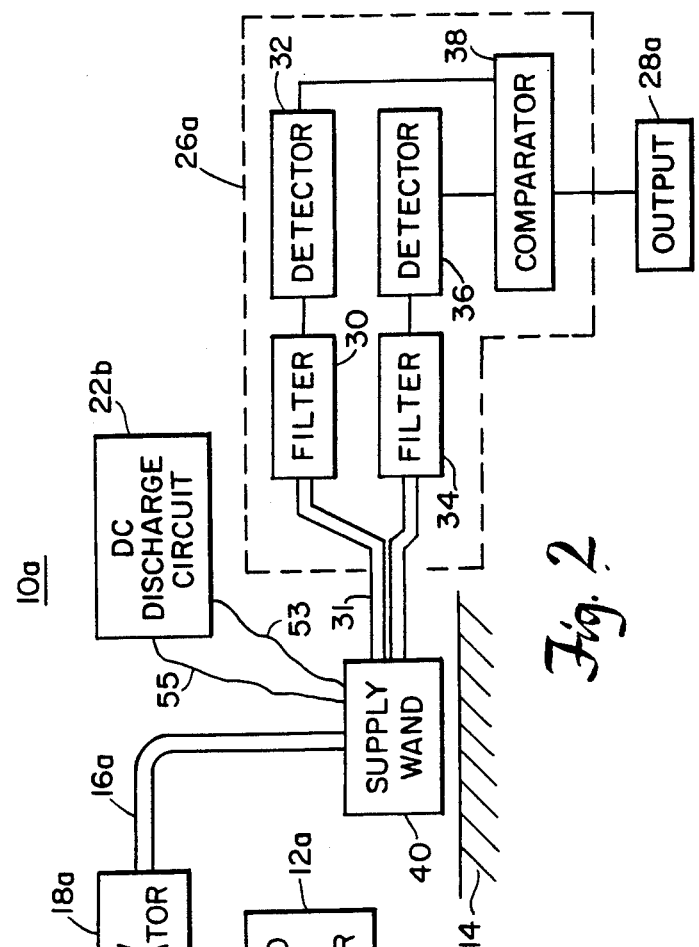
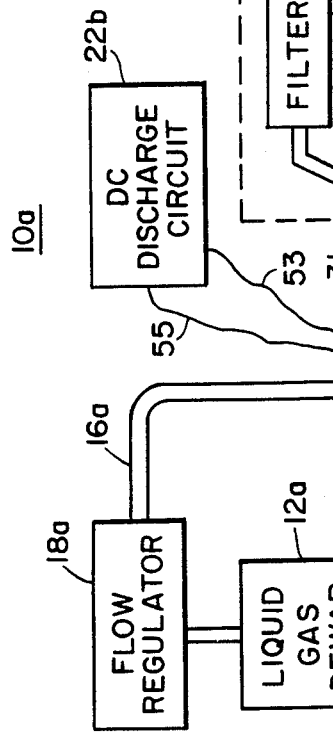
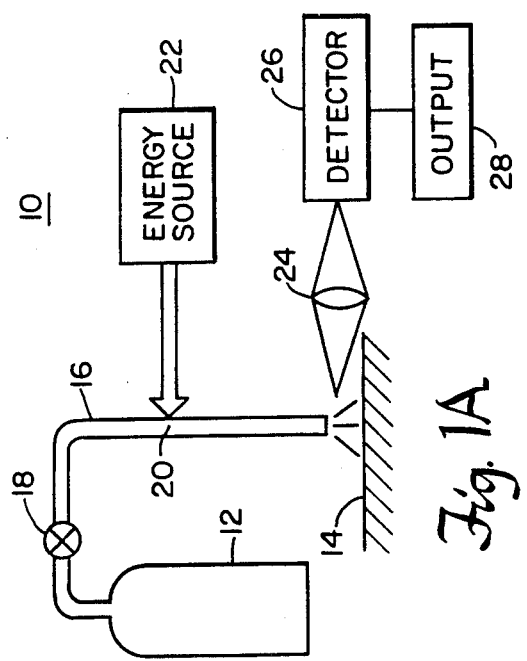

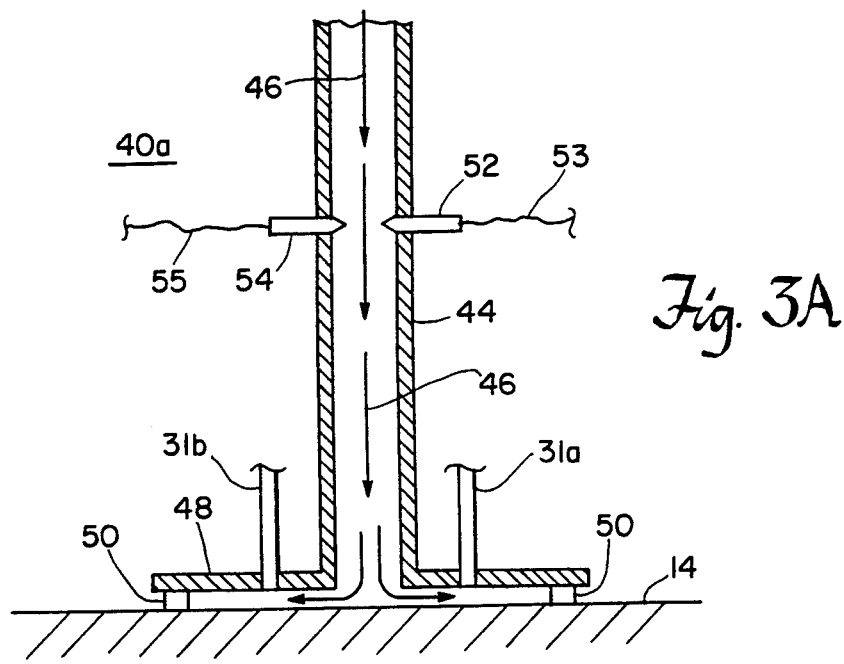
*Fig.* 3A
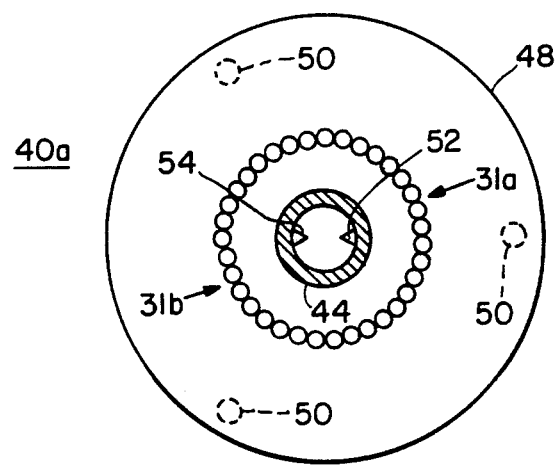
*Fig.* 3B
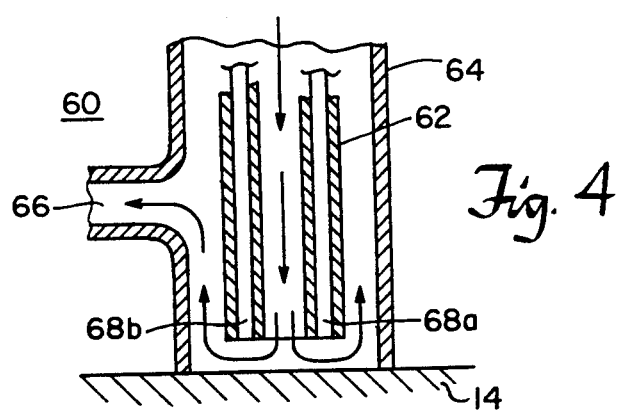
*Fig.* 4

SURFACE CONTAMINATION SENSOR

GOVERNMENT RIGHTS

The invention was made with government support under Contract No. NAS10-11459 awarded by the National Aeronautics and Space Administration. The government has certain rights in this invention.

FIELD OF INVENTION

This invention relates to a sensor for detecting the presence of organic contamination on a surface.

BACKGROUND OF INVENTION

There are many situations in which it is desirable to sense the presence of and/or quantity of contaminants such as hydrocarbons or other non-volatile residue on surfaces. For example, satellites or other spacecraft contain many critical surfaces which must be kept strictly clean prior to launch to avoid degradation of optical, heat rejection, or other properties. In these situations, in addition to insuring cleanliness of the environment, it is also desirable to monitor directly the cleanliness of the surfaces. Large particles on the surfaces are detectable by optical scattering techniques. For detection and measurement of molecular contamination such as non-volatile residue, typically consisting of a hydrocarbon film such as an oil film, the detection is typically accomplished by mounting a "witness" plate or surface near the surface to be monitored. Periodically, this witness plate is removed and analyzed for contaminants which it and, presumably, the surface of interest, may have acquired. This analysis typically involves washing the witness plate with solvent and analyzing the solvent for contaminants. Alternatively, the surface may be analyzed for contaminants by spectrometry.

Contaminant surface deposition real-time monitoring may be accomplished with quartz crystal microbalances placed proximate the surface being monitored for the duration of the possible contaminant deposition. These quartz crystal devices, however, are sensitive to humidity fluctuations, and so are best suited for vacuum environments.

In another scheme for detecting the presence of surface contaminants, the surface is irradiated with ultraviolet light to ionize the contaminants, and an extremely sensitive surface current detection device is used to detect current flow from the ionization, which is related to the amount and type of contaminant. In such systems, however, the surface to be monitored must be measured prior to contaminant exposure, when it is absolutely clean, to provide the comparison current necessary for contaminant sensing.

SUMMARY OF INVENTION

It is therefore an object of this invention to provide a real-time surface contamination sensor.

It is a further object of this invention to provide such a sensor which is portable.

It is a further object of this invention to provide such a sensor which does not require the removal of parts or an extraneous surface from the contaminated atmosphere for testing.

It is a further object of this invention to provide such a sensor which may be used directly in the ambient environment.

It is a further object of this invention to provide such a sensor which can detect and quantify the contaminant level.

It is a further object of this invention to provide such a sensor which does not require the use of solvents.

It is a further object of this invention to provide such a sensor which does not require a mass spectrometer.

It is a further object of this invention to provide such a sensor which can measure both volatile and non-volatile contaminants.

This invention results from the realization that a direct reading, real time surface contamination sensor may be accomplished by sweeping an activated gas over the surface to be sensed and detecting the optical emission from the gas after it passes over the surface in a selected wavelength band characteristic of the contaminant present on the surface.

This invention features an ambient surface contamination sensor including means for supplying a gas to a surface being sensed; means for energizing the gas before it reaches the surface for transferring the energy to the contaminant or vapor originating therefrom; means for detecting the optical emission from the gas passed over the surface within a selected wavelength band characteristic of the presence on the surface of the contaminant; and means for indicating the presence of the contaminant on the surface. There may further be included means for vaporizing the contaminant from the surface into the active gas to allow the quantification of the contaminant level on the surface being sensed.

Preferably, the gas is supplied to the surface with a gas supply wand which delivers a gas stream to the surface. This may be accomplished with a gas flow tube with the gas-emitting opening proximate the surface, along with means for directing gas flow from the opening across the surface being sensed. There is preferably further included means for maintaining the opening a desired distance from the surface being sensed.

There may further be included means for regulating the gas flow to the surface. Preferably, the gas is nitrogen. The gas may be energized with a dc discharge, a microwave discharge, a laser, an rf discharge, a hot wire, or any other source for supplying energy to the gas to create an activated gas which is reactive with the contaminants.

In a preferred embodiment, the means for detecting the optical emission from the surface includes means for collecting light emitted from the gas stream as or after it contacts the surface. This may be accomplished with one or more optical fibers having light-collecting ends proximate the surface being sensed. The means for indicating the presence of the contaminant may include means for discriminating between the emissions from the gas and the emissions from the contaminants, which may be accomplished by filtering separately the gas emission and the contaminant emission from the detected emission to create a contamination emission signal and a gas emission signal. In that case, the two signals may be compared to create a normalized contamination emission signal indicative of the presence on the surface of the contaminant, and further indicative of the vapor pressure of that contaminant.

To determine the quantity of the contaminant on the surface being sensed, there is preferably included a means for vaporizing the contaminant from the surface into the gas passing over the surface, and a means for resolving the optical emission after the contaminant is vaporized. The contaminant may be vaporized with a laser.

DISCLOSURE OF PREFERRED EMBODIMENT

Other objects, features and advantages will occur to those skilled in the art from the following description of a preferred embodiment and the accompanying drawings, in which:

FIG. 1A is a simplified, schematic diagram of the surface contamination sensor according to this invention;

FIG. 1B is a schematic diagram of an energy source for the sensor of FIG. 1A;

FIG. 2 is a more detailed schematic diagram of the surface contamination sensor of this invention employing a DC discharge to activate the gas flow;

FIGS. 3A and 3B are side cross-sectional and top plan views of a gas supply wand for the sensor of this invention;

FIG. 4 is an alternative supply wand to that disclosed in FIGS. 3A and 3B;

Figure 5:
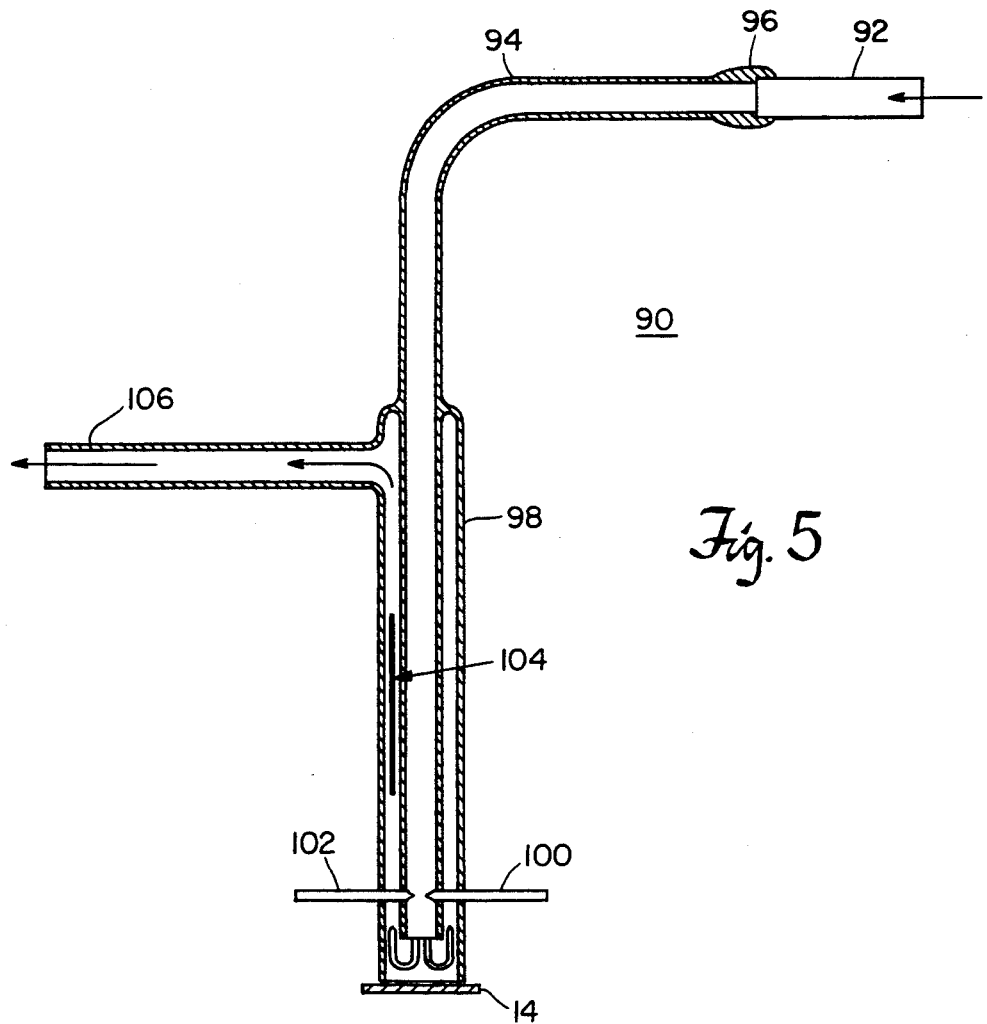
FIG. 5 is another alternative supply wand for use with a monochromator detector.

This invention may be accomplished in an ambient surface contamination sensor in which a gas such as nitrogen is energized and flowed over the surface to be sensed to transfer energy to the contaminant or vapor originating from the contaminant, and the optical emission from the gas within a selected wavelength band characteristic of the presence on the surface of the contaminant is detected to indicate the presence of the contaminant.

There is shown in FIG. 1A ambient surface contamination sensor 10 according to this invention for detecting the presence on surface 14 of a layer of contaminant being sensed. In most situations the contaminants are hydrocarbons or other non-volatile organic residues. Sensor 10, however, detects a small quantity of contaminant vapor residing above the contaminant layer. Accordingly, the sensor may also be used to detect surface outgassing, for example to determine if a surface is fully cured or free of solvent. Sensor 10 includes gas source 12 for supplying gas through line 16 to surface 14. Valve 18 controls the flow rate and/or gas pressure delivered to surface 14. Energy source 22 energizes the gas flowing through activation region 20 for supplying an activated gas to the surface; this gas is capable of transferring energy to the contaminant. In a preferred embodiment, the gas is nitrogen, although pure argon or helium may also be used. When nitrogen is used, the active species include nitrogen atoms and metastable, high energy, molecules.

When the active gas reaches surface 14 being sensed, the active gas species react with the contaminant vapor residing above the contaminant layer to form an excited product, which emits at a wavelength band different from the active gas emission wavelength bands. When the contaminant is an organic material and the active gas is nitrogen, excited cyanogen (CN) is formed as a product. Lens 24 collects light emitted from the surface region and focuses it on detector 26, which may include a monochromator and photomultiplier tube for detecting emissions at the CN or other excited product wavelength band. The output of detector 26 is supplied to output device 28 for indicating the presence of contaminants on surface 14 when the excited product emission is detected.

There are many ways in which energy may be supplied to the flowing gas stream before it reaches the surface to be sensed in order to activate the gas into the required high-energy reactive state. For example, as shown in FIG. 1B, energy source 22a may comprise microwave source 70 and microwave wave guide 72 for supplying microwave energy to activation region 20a of gas flow tube 16 passing through waveguide 72. Other means of energizing the gas include rf induction, lasers, and hot filament excitation, as well as excitation by DC discharge shown in FIGS. 2 and 3A. It is simply necessary to in some manner transfer energy to the flowing gas to create an activated or energized gas which is reactive with the contaminant for creating product species which emit at wavelength bands which do not coincide with the emission bands of the activated gas.

Surface contamination sensor 10a according to this invention employing a DC discharge gas excitation means is shown in FIG. 2. In this embodiment, ultrapure gas is provided with relative ease and low cost to surface 14 being sensed by employing a cryogenic liquid gas held in dewar 12a. Since cyrogenic liquid gases typically have a much higher vapor pressure than the contaminants therein, using a cyrogenic liquid gas is a simple means of supplying a very pure gas stream for washing the surface being sensed. If liquid nitrogen is used, the hydrocarbon contaminants found at low levels in commercially available gaseous nitrogen have such low vapor pressures that they are virtually non-existent in the gas flowing from dewar 12a. As a result, there are virtually no hydrocarbon contaminants in the active gas supplied to surface 14 and therefore there will be no spurious contaminant measurements.

Flow regulator 18a provides a desired flow rate and/or pressure of nitrogen gas through line 16a to supply wand 40 which distributes the gas onto surface 14. DC discharge circuit 22b provides a continuous direct current discharge through lines 53 and 55 to electrodes, not shown, in supply wand 40 for activating the gas. Detector circuit 26a receives the light emissions from the activated gas as it impinges on, or after it has impinged on, surface 14. In this embodiment, the detected light is carried from the region of surface 14 being sensed to detection circuit 26a by fiber optic cable 31, which supplies the radiation to both nitrogen-band filter 30 and cyanogen-band filter 34. The most intense CN band has a broad peak around 385 nm, and there is a nitrogen band at 380 nm. Thus, filter 30 may let the 380 nm light pass and filter 34 may let the 385 nm light pass for supplying to detectors 32 and 36 light representing the emission from the nitrogen and cyanogen, respectively. The signals from detectors 32 and 36 are supplied to comparator circuit 38, which divides the CN signal by the nitrogen signal and supplies the resulting signal representative of the normalized strength of the CN signal to output 28a. The use of the nitrogen signal to normalize the CN is not required, but may reduce fluctuations in the CN signal caused by variations in the degree of excitation of the active nitrogen.

In experiments conducted with hydrocarbon contaminants such as fingerprints and vacuum pump oil, it has been found that the strength of this normalized CN signal is related to the vapor pressure of the contaminant. From this fact it is inferred that the reaction between the activated gas species and the hydrocarbons occurs in the gas phase; that is, the hydrocarbons evaporate or outgas from the surface being sensed into the activated gas stream, where they react with the active nitrogen to form excited cyanogen—a short-lived species which emits at the 385 nm wavelength band. It is believed that this CN signal should be present at all points at the surface region and downstream thereof until all of the hydrocarbons swept up in the flow have been decomposed to form the excited CN. Presuming this is true, the strongest signal should be found directly above the sample surface. However, the spurious CN emission from organic contaminants in the supply gas, or contaminants which may otherwise enter the gas stream before it contacts the surface, would be strong in this region due to the fact that the spurious CN emissions would occur close to the gas activation region. However, by the time the gas moves slightly downstream of the surface, the gas activation region will be out of view of the detectors and the spurious emissions will have effectively disappeared. Thus, the most desirable point at which to sense the emissions is just slightly downstream of the surface being sensed.

One supply wand design for accomplishing these objectives is shown in FIGS. 3A and Wand 40a includes gas flow tube 44 for conducting the gas to be activated in the direction of arrows 46 from the gas source, not shown, toward and across surface 14 being sensed. Electrodes 52 and 54 are DC discharge electrodes responsive to a DC discharge circuit such as circuit 22b, FIG. 2, for continuously passing an electric arc through the gas to activate the gas. Wand 40a also includes annular plate 48 for directing the flow radially outwardly from tube 44 across surface 14. Fiber optic cables 31a and 31b are spaced radially around tube 44 for detecting the emissions from the gas as it passes over surface 14 being sensed. Spacer feet 50 are attached to the bottom of plate 48 for maintaining a known distance between surface 14 and plate 48 for repeatable measurements while minimizing the physical contact between the wand and the sensed surface. In this embodiment, set 31a of fiber optic cables is passed to one of the nitrogen or cyanogen detectors and set 31b of cables is passed to the other detector for providing the signals for detection circuitry 26a, FIG. 2. There are typically a number of cables as shown in FIG. 3B. The cables in set 31a may comprise every other cable in the entire set, and set 31b the remaining cables to eliminate any inaccuracies due to uneven gas flow distribution.

An alternative wand design employing such fiber optic sensing is shown in FIG. 4, which is merely illustrative of the wands which may be used in the sensor of this invention. Wand 60 includes outer tube 64 containing inner gas flow tube 62 with fiber optic bundles 68a and 68b held within the walls of tube 62. Gas flow tube 62 supplies gas to surface 14; gas flow is depicted by the arrows. In this embodiment, outer tube 64 rests on or near surface 14 and the gas flows through tube 62 onto surface 14 and out of tube 64 through opening 66. Fiber optic bundles 68a and 68b are oriented to view the portions of surface 14 which are not directly below tube 62 so that emissions from the arc discharge and the spurious emissions from organic contaminants are not detected by the detection circuitry. It is important only that the field of view of the fiber optic cables for detecting the gas emissions at or near the surface being sensed and supplying signals to the gas and contaminant sensing circuitry be directed away from the arc discharge and/or the spurious contaminant emissions. It is also desirable to fashion a probe in which the flow of active gas is arranged in such a manner as to exclude air from the surface being sensed so that there are no emissions from other contaminants or gases present in the air. This is accomplished in part by using an atmospheric or slightly higher pressure gas source for supplying the gas, preferably nitrogen, to be activated and flowed over the surface being sensed, greatly simplifying the sensor device and maintaining its low cost.

A probe design which may be used with a monochromator or another means of dispersing light is shown in FIG. 5. Wand 90 includes outer glass tube 98 with inner glass gas supply tube 94 held therein. The gas to be activated is supplied through tube 92, which is preferably a metal tube which will not release any organic contaminants into the gas flow, using glass to metal seal 96 for passing the gas into tube 94. Electrodes 100 and 102 pass the discharge through the gas flowing in tube 94, which then impinges on surface 14 and turns back up and passes out through exhaust line 106. The monochromator, not shown, is raised above surface 14 so that the image of its slit 104 lies above, thus downstream of, the spark discharge and surface 14. The imaged area lies to the side of wand 90 so that more light might be obtained over a longer integrated viewing path. When using a monochromator, it may be tuned alternately between the 380 nm nitrogen band and the 385 nm CN band to provide the two signals used.

Figure 6:
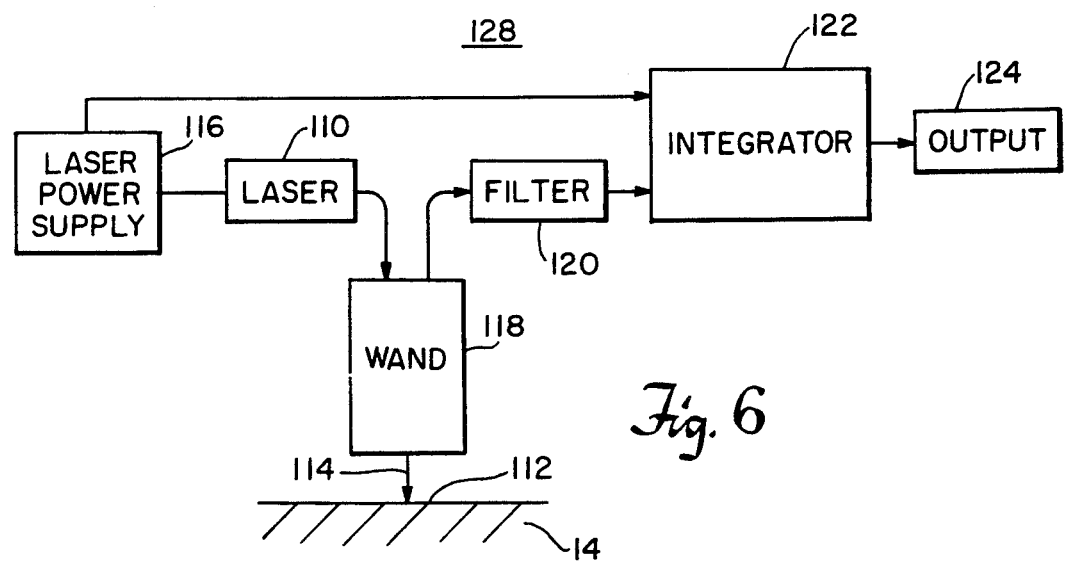
FIG. 6 is a schematic diagram of an alternative surface contamination sensor according to this invention employing a laser to vaporize the surface contaminants.

An alternative embodiment of the surface contamination sensor according to this invention for detecting non-volatile residue, and for quantifying detected contaminants is depicted in FIG. 6, in which sensor 128 includes gas supply wand 118. The gas supply and gas activation circuitry are not shown in this drawing. Laser 110 for supplying laser beam 114 to area 112 of surface 14 being sensed is controlled by laser power supply 116 for utilizing laser-induced thermal desorption of the contaminant in area 112 into the flow of active gas from wand 118. In this embodiment, irradiation of surface area 112 with a single laser pulse of the proper intensity well below the surface damage threshold causes complete desorption or evaporation of the organic contamination lying within the area of the laser beam. Accordingly, with use of the laser or another means of instantaneously evaporating the organic contaminant, the sensor may be used to detect non-volatile components and may also be used to quantify the contaminant present in area 112 being sensed. In a preferred embodiment, the laser is a pulsed Nd:YAG laser delivering approximately 20 mJ of optical energy per pulse in an unfocused beam of about 3 mm in diameter.

Single filter 120, which passes only the CN or other contaminant product emission band, is used to supply a signal to integrator 122. Integrator 122 is responsive to laser power supply 116 for determining the detected signal strength immediately after the laser pulse. The result is a large spike signal representative of the CN emissions from all of the organic molecules which were present in the portion of area 112 irradiated by the laser beam. Such time gating of the signal detection also provides better signal sensitivity. Since the strength of the laser is set so as to evaporate all of the contaminant from the irradiated portion of area 112 being sensed, the signal supplied to output device 124 is a measure of the total amount of hydrocarbon contaminant present in area 112, rather than the qualitative measurement from the system without the thermal desorption means. It should be understood that the laser head is preferably mounted within the wand to provide a one-piece, portable probe design which provides the ability to quickly and easily measure surface contaminants in situ. Alternatively, the beam from the laser head may be sent to the wand via a fiber optic or optical waveguide; the beam emerges from the waveguide within the wand and falls onto the sample surface.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An ambient surface contamination sensor, comprising:
    means for supplying a gas to a surface being sensed;
    means for energizing the gas before it reaches the surface for transferring energy to surface contaminants;
    means for detecting the optical emission from the gas passed over the surface within a selected wavelength band characteristic of the presence on the surface of the contaminant; and
    means, responsive to said means for detecting, for indicating the presence of the contaminant on the surface.

2. The contamination sensor of claim 1 in which said means for supplying a gas includes a gas supply wand for delivering a gas stream to the surface.

3. The contamination sensor of claim 2 in which said wand includes a gas flow tube with a gas emitting opening.

4. The contamination sensor of claim 3 in which said wand further includes means for directing gas flow from said opening across the surface being sensed.

5. The contamination sensor of claim 4 in which said means for directing gas flow includes an annular plate proximate said opening.

6. The contamination sensor of claim 3 further including means for maintaining said opening a desired distance from the surface being sensed 7. The contamination sensor of claim 1 in which said means for supplying a gas includes means for regulating the gas flow to the surface.

8. The contamination sensor of claim 1 in which said means for energizing includes means for creating a dc discharge in the gas flow.

9. The contamination sensor of claim 1 in which said means for energizing includes means for supplying an electrodeless discharge to the gas flow.

10. The contamination sensor of claim 1 in which the gas is nitrogen.

11. The contamination sensor of claim 1 in which said means for detecting includes means for collecting light emitted from the gas stream after it contacts the surface.

12. The contamination sensor of claim 11 in which said means for collecting includes optical fiber means having a light-collecting end proximate the surface being sensed.

13. The contamination sensor of claim 1 in which said means for indicating includes means for discriminating between emissions from the gas and emissions from the contaminants.

14. The contamination sensor of claim 13 in which said means for discriminating includes means for filtering the gas emission from the detected emission to create a contamination emission signal.

15. The contamination sensor of claim 14 in which said means for indicating further includes means for filtering the contaminant emission from the detected emission to create a gas emission signal.

16. The contamination sensor of claim 15 in which said means for indicating further includes means for comparing said contamination emission signal to said gas emission signal to create a normalized contamination emission signal indicative of the presence on the surface of the contaminant.

17. The contamination sensor of claim 1 further including means for determining the quantity of contaminant on the surface being sensed.

18. The contamination sensor of claim 17 in which said means for determining includes means for vaporizing the contaminant from the surface into the gas passing over the surface.

19. The contamination sensor of claim 18 in which said means for determining further includes means, responsive to said means for detecting, for resolving the optical emission after the contaminant is vaporized.

20. The contamination sensor of claim 18 in which said gas includes nitrogen.

21. The contamination sensor of claim 18 in which said means for vaporizing includes a laser.

22. An ambient surface contamination sensor, comprising:
    means for supplying a gas stream to a surface being sensed;
    means for energizing the gas before it reaches the surface to create an active gas for transferring energy to the surface contaminants;
    means for detecting the optical emission from the gas after it contacts the surface at both a first wavelength band characteristic of the gas and a second wavelength band characteristic of the presence on the surface of the contaminant;
    means, responsive to said means for detecting, for resolving the relative strengths of the emissions at the first and second bands; and
    means, responsive to said means for resolving, for indicating the presence on the surface of the contaminant.

23. An ambient surface contamination sensor, comprising:
    means for supplying a gas stream to a surface being sensed;
    means for energizing the gas before it reaches the surface to create an active gas for transferring energy to the contaminants;
    means for vaporizing the contaminant from the surface into the active gas;
    means for detecting the optical emission from the gas after the contaminant is vaporized at a wavelength band characteristic of the presence on the surface of the contaminant;
    means, responsive to said means for detecting, for resolving the strength of the emission; and
    means, responsive to said means for resolving, for determining the quantity of contamination on the surface.

* * * * *